United States Patent [19]

Schmidt et al.

[11] 4,213,984
[45] Jul. 22, 1980

[54] 11-(PIPERAZINO-ACETYL)-5,11-DIHYDRO-6H-PYRIDO[2,3-b][1,4]BENZODIAZEPIN-6-ONES AND SALTS THEREOF

[75] Inventors: Günther Schmidt; Matyas Leitold, both of Biberach an der Riss, Fed. Rep. of Germany

[73] Assignee: Boehringer Ingelheim GmbH, Ingelheim am Rhein, Fed. Rep. of Germany

[21] Appl. No.: 907,888

[22] Filed: May 19, 1978

[30] Foreign Application Priority Data

May 31, 1977 [DE] Fed. Rep. of Germany ....... 2724434

[51] Int. Cl.² .................... A61K 31/55; C07D 403/06
[52] U.S. Cl. ............................. 424/250; 260/239.3 T
[58] Field of Search ................. 260/239.3 T; 424/250

[56] References Cited

U.S. PATENT DOCUMENTS

3,660,380  5/1972  Schmidt et al. ............... 260/239.3 T

*Primary Examiner*—John M. Ford
*Assistant Examiner*—Robert T. Bond
*Attorney, Agent, or Firm*—Hammond & Littell, Weissenberger & Muserlian

[57] ABSTRACT

Compounds of the formula

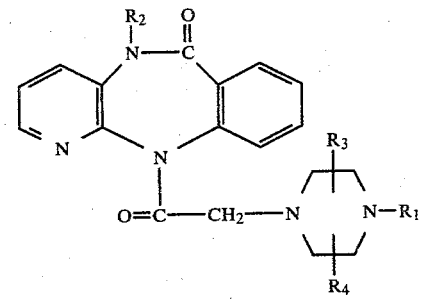

wherein
$R_1$ is alkyl of 3 to 12 carbon atoms; unsaturated aliphatic hydrocarbyl of 3 to 20 carbon atoms comprising 1 to 3 double bonds and/or one triple bond; phenyl(alkyl of 2 to 4 carbon atoms); methylenedioxybenzyl; chlorobenzyl; indan-5-ylmethyl; indan-3-ylmethyl; phenyl(alkenyl of 2 to 4 carbon atoms); cycloalkyl of 5 to 7 carbon atoms; (cycloalkyl of 3 to 10 carbon atoms)methyl; (methylcycloalkyl of 4 to 11 carbon atoms)methyl; morpholino(alkyl of 2 to 3 carbon atoms); pyrrolidino(alkyl of 2 to 3 carbon atoms); piperidino (alkyl of 2 to 3 carbon atoms); 4-methylpiperazino(alkyl of 2 to 3 carbon atoms); or, when $R_3$ and/or $R_4$ are methyl or ethyl, also methyl or ethyl;
$R_2$ is hydrogen, methyl or ethyl; and
$R_3$ and $R_4$ are each hydrogen, methyl or ethyl;

and non-toxic, pharmacologically acceptable acid addition salts thereof. The compounds as well as the salts are useful as anti-ulcerogenics and secretion inhibitors.

11 Claims, No Drawings

11-(PIPERAZINO-ACETYL)-5,11-DIHYDRO-6H-PYRIDO[2,3-B][1,4]BENZODIAZEPIN-6-ONES AND SALTS THEREOF

This invention relates to novel 11-(piperazino-acetyl)-5,11-dihydro-6H-pyrido[2,3-b][1,4]benzodiazepin-6-ones and non-toxic acid addition salts thereof, as well as to various methods of preparing these compounds.

More particularly, the present invention relates to a novel class of compounds represented by the formula

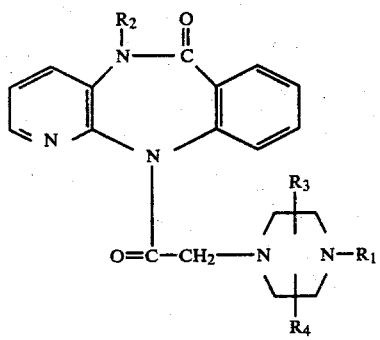 (I)

wherein
R$_1$ is alkyl of 3 to 12 carbon atoms; unsaturated aliphatic hydrocarbyl of 3 to 20 carbon atoms comprising 1 to 3 double bonds and/or one triple bond; phenyl(alkyl of 2 to 4 carbon atoms); methylenedioxybenzyl; chlorobenzyl; indan-5-ylmethyl; indan-3-ylmethyl; phenyl(alkenyl of 2 to 4 carbon atoms); cycloalkyl of 5 to 7 carbon atoms; cycloalkyl of 3 to 10 carbon atoms)methyl; (methylcycloalkyl of 4 to 11 carbon atoms)methyl; morpholino(alkyl of 2 to 3 carbon atoms); pyrrolidino(alkyl of 2 to 3 carbon atoms); piperidino (alkyl of 2 to 3 carbon atoms); 4-methylpiperazino (alkyl of 2 to 3 carbon atoms); or, when R$_3$ and/or R$_4$ are methyl or ethyl, also methyl or ethyl;

R$_2$ is hydrogen, methyl or ethyl; and

R$_3$ and R$_4$ are each hydrogen, methyl or ethyl; and non-toxic, pharmacologically acceptable acid addition salts thereof.

The compounds embraced by formula I may be prepared by the following methods:

Method A

By reacting an 11-haloacetyl-5,11-dihydro-6H-pyrido[2,3-b][1,4]benzodiazepin-6-one of the formula

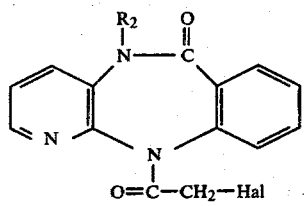 (II)

wherein R$_2$ has the same meanings as in formula I, and Hal is halogen, with a piperazine of the formula

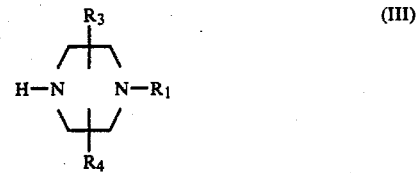 (III)

wherein R$_1$, R$_3$ and R$_4$ have the same meanings as in formula I.

The reaction is advantageously carried out in an inert solvent, optionally in the presence of an acid-binding agent, and at elevated temperatures, preferably at the boiling point of the solvent which is used. Preferred solvents are alcohols, such as ethanol, n-propanol or isopropanol; ketones, such as acetone; ethers, such as dioxane or tetrahydrofuran; or aromatic hydrocarbons, such as benzene or toluene. It is advantageous to provide the piperazine of the formula III in a sufficient excess to bind the liberated hydrogen halide; however, other hydrogen halide-binding agents, as for example alkali metal carbonates, alkali metal bicarbonates or tertiary organic amines, such as triethylamine, pyridine or dimethylaniline, may be added to the reaction mixture.

Method B

By reacting a 5,11-dihydro-11-[(1-piperazinyl)acetyl]-6H-pyrido[2,3-b][1,4]benzodiazepin-6-one of the formula

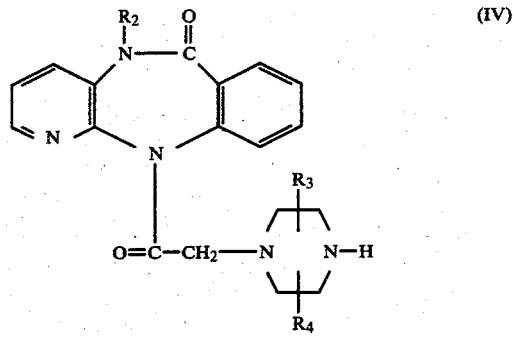 (IV)

wherein R$_2$, R$_3$ and R$_4$ have the same meanings as in formula I, with halide of the formula R$_1$-Hal (V)

wherein R$_1$ and Hal have the meanings previously defined.

The reaction is carried out in an inert solvent, preferably in an alcohol, such as ethanol, n-propanol or isopropanol; in an ether, such as dioxane or tetrahydrofuran; or in a ketone, such as acetone; and at elevated temperatures, preferably at the boiling point of the solvent which is used. It is recommended to bind the liberated hydrogen halide with a hydrogen halide-binding agent, as for example with alkali metal carbonates, alkali metal bicarbonates or tertiary organic amines, such as triethylamine, pyridine or dimethylaniline.

The compounds of the formula I are organic bases and therefore form acid addition salts with inorganic or organic acids. Examples of non-toxic, pharmacologically acceptable acid addition salts are those formed with hydrochloric acid, hydrobromic acid, sulfuric acid, phosphoric acid, acetic acid, fumaric acid, citric acid, maleic acid, succinic acid, oxalic acid, 8-chloro-theophylline or the like.

The starting compounds of the formula II can be prepared by reacting a 5,11-dihydro-6H-pyrido[2,3-b][1,4]-benzodiazepin-6-one of the formula

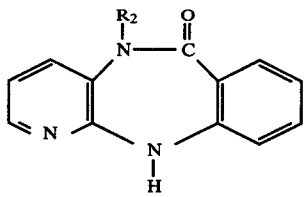

wherein $R_2$ has the same meanings as in formula I, with a haloacetyl halide of the formula

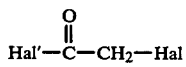

wherein Hal and Hal' are each chlorine, bromine or iodine.

The reaction is preferably carried out in an inert solvent in the presence of a hydrogen halide-binding agent at elevated temperatures, preferably at the boiling point of the solvent which is used. Suitable solvents are aromatic hydrocarbons, such as benzene, toluene or xylene; or ethers, such as diethylether, dipropyl-ether or preferably cyclic ethers, like dioxane. Suitable hydrogen halide-binding agents are tertiary organic bases such as triethylamine, N,N-dimethylaniline or pyridine, or also inorganic bases, like alkali metal carbonates or alkali metal bicarbonates. The processing of the reaction mixture is carried out in the usual way; the yields amount up to 90% of theory. The formed haloacetyl compounds of the formula II are mostly well crystallizable substances (see also German Pat. No. 1,795,183).

The compounds of the formula VI are known from the literature (see German Pat. Nos. 1,179,943 and 1,204,680).

The compounds of the formula IV are obtained by reacting a compound of the formula II with N-benzyl-piperazine in a solvent, such as ether, dioxane, ethanol, propanol or benzene, under reflux. A crystalline precipitate is thus obtained, which is suction-filtered off and isolated, for example, as the hydrochloride. The free base of the thus formed compound of the formula

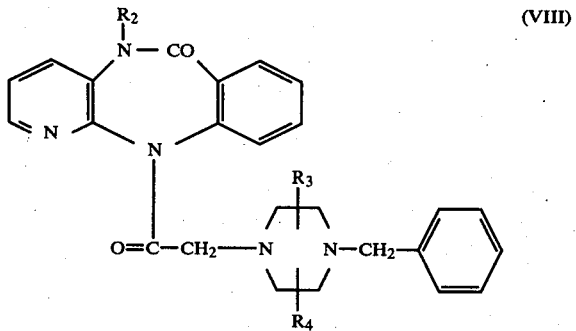

wherein $R_2$, $R_3$ and $R_4$ have the meanings previously defined, is subsequently dissolved in an alcohol, such as in methanol, and hydrogenated in the presence of palladium-on-charcoal at 20° to 80° C. preferably at 50° C., and a hydrogen pressure of 1 to 100 atmospheres, preferably 50 atmospheres; subsequently, the corresponding compound of the formula IV is isolated from the reaction mixture.

Specific examples of the various types of radicals included in the definition of $R_1$ are the following:

Alkyl- methyl, ethyl, propyl, isopropyl, n-butyl, sec.-butyl, isobutyl, tert.butyl, neopentyl, isopentyl, n-pentyl, 1-methyl-butyl, 3-methyl-butyl, n-hexyl, 4-methyl-pentyl, 2-ethyl-butyl, 3,3-dimethyl-butyl, heptyl, octyl, nonyl, decyl, undecyl and dodecyl;

Unsaturated aliphatic hydrocarbyl- 2-methyl-allyl, allyl, but-2-enyl, 1-methyl-allyl, pent-4-enyl, 3-methyl-but-2-enyl, n-hex-5-enyl, n-hept-6-enyl, farnesyl, neryl, geranyl, citronellyl, phytyl and propargyl;

Phenylalkyl- 2-phenylethyl, 1-phenyl-ethyl, 3-phenylpropyl, 2-phenylpropyl, 1-phenyl-propyl, phenyl-isopropyl or 4-phenyl-butyl;

Phenylalkenyl- cinnamyl, phenyl-ethylene, 4-phenyl-but-2 (or -3) enyl or an isomer thereof with the phenyl group in 2- or 3-position;

Cycloalkyl- cyclopentyl, cyclohexyl and cycloheptyl;

Cycloalkylmethyl- adamantyl-, cycloheptyl-, cyclohexyl-, cyclopentyl-, cyclobutyl-, cyclopropyl- and bicyclo[2,2,1]hept-2-yl-methyl.

The following examples illustrate the present invention and will enable others skilled in the art to understand it more completely. It should be understood, however, that the invention is not limited solely to the particular examples given below.

EXAMPLE 1

5,11-Dihydro-11-{[4-(2-methyl-allyl)-1-piperazinyl]acetyl}-6H-pyrido[2,3-b][1,4]benzodiazepin-6-one by method A 8.62 gm of 11-chloroacetyl-5,11-dihydro-6H-pyrido[2,3-b][1,4]-benzodiazepin-6-one, 3.5 gm of sodium carbonate and 4.6 gm of 1-(2-methyl-allyl)-piperazine were refluxed in 100 ml of absolute ethanol for 2 hours. Then, the reaction mixture was suction-filtered while still hot, and the filtrate was evaporated to a volume of 40 ml and cooled. The precipitated crystals were recrystallized from ethanol in the presence of activated charcoal, yielding 75% of theory of the compound of the formula

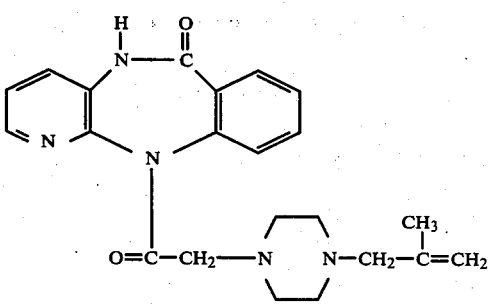

which had a melting point of 205°–207° C.

EXAMPLE 2

5,11-Dihydro-11-{[4-(3-methyl-but-2-enyl)-1-piperazinyl]acetyl}-6H-pyrido[2,3-b][1,4]benzodiazepin-6-one dihydrochloride 8.62 gm of 11-chloroacetyl-5,11-dihydro-6H-pyrido[2,3-b][1,4]-benzodiazepin-6-one, 3.5 gm of sodium carbonate and 5.07 gm of 1-(3-methyl-but-2-enyl)-piperazine [$R_1$=—$CH_2$—CH=C($CH_3$)$_2$] were refluxed in 100 ml of isopropanol for 2.5 hours. Then, the reaction mixture was suction-filtered while still hot, and the filtrate evaporated to a volume of 40 ml and cooled. The precipitated crystals were dissolved, while heating, in 100 ml of absolute ethanol, and the calculated quantity of concentrated hydrochloric acid was added. Upon cooling, the dihydrochloride crystallized out.

M.p.: 208°–211° C.
Yield: 70% of theory.

EXAMPLE 3

5,11-Dihydro-11-{[4-(2,2-dimethyl-propyl)-1-piperazinyl]acetyl}-6H-pyrido[2,3-b][1,4]benzodiazepin-6-one 7.15 gm of 11-chloroacetyl-5,11-dihydro-6H-pyrido[2,3-b][1,4]benzodiazepin-6-one, 2.9 gm of potassium carbonate and 4.5 gm of 1-(2,2-dimethyl-propyl)-piperazine were refluxed for 5 hours in 100 ml of absolute ethanol. Then, the hot reaction mixture was suction filtered. The crystals which precipitated out of the filtrate were then recrystallized from isopropanol in the presence of activated charcoal.

M.p.: 232°–234° C.
Yield: 40% of theory.

EXAMPLE 4

11-[(4-Allyl-1-piperazinyl)acetyl]-5,11-dihydro-6H-pyrido[2,3-b]-[1,4]benzodiazepin-6-one 8.62 gm of 11-chloroacetyl-5,11-dihydro-6H-pyrido[2,3-b][1,4]benzodiazepin-6-one and 8.3 gm of 1-allyl-piperazine were refluxed in 100 ml of ethanol for 2 hours. The reaction mixture was then evaporated, and the crystalline precipitate was subsequently recrystallized from 30 ml of isopropanol and then from 94% ethanol in the presence of activated charcoal.

M.p.: 230°–233° C.
Yield: 47% of theory.

EXAMPLE 5

11-{[4-(n-But-2-enyl)-1-piperazinyl]acetyl}-5,11-dihydro-6H-pyrido[2,3-b][1,4]benzodiazepin-6-one dihydrochloride dihydrate 8.62 gm of 11-chloroacetyl-5,11-dihydro-6H-pyrido[2,3-b][1,4]-benzodiazepin-6-one and 8.7 gm of 1-(n-but-2-enyl)-piperazine ($R_1$=—$CH_2$—CH=CH—$CH_3$) were refluxed in 100 ml of dioxane for 3 hours, and the reaction mixture was then evaporated in vacuo. The residue was purified on a silica gel column, and the obtained oily base was dissolved in 70 ml of hot isopropanol. The solution was acidified with hydrochloric acid, whereby the dihydrochloride crystallized out which was recrystallized from 94% ethanol. The obtained crystals included 2 mols of water of crystallization and melted at M.p.: 207°–210° C.
Yield: 35% of theory.

EXAMPLE 6

5,11-Dihydro-11-[(4-neryl-1-piperazinyl)acetyl]-6H-pyrido[2,3-b][1,4]benzodiazepin-6-one dihydrochloride was prepared from 5.8 gm of 11-chloroacetyl-5,11-dihydro-6H-pyrido-[2,3-b][1,4]benzodiazepin-6-one, 2.4 gm of sodium carbonate and 5.3 gm of 1-neryl-piperazine in 100 ml of absolute ethanol in analogy to Example 1. The obtained raw product was purified on a silica gel column and converted into the dihydrochloride in absolute ethanol with concentrated hydrochloric acid. After recrystallization from absolute ethanol: M.p.: 188°–191° C.

Yield: 65% of theory.

EXAMPLE 7

5,11-Dihydro-11-{[4-(α-methylbenzyl)-1-piperazinyl]acetyl}-6H-pyrido[2,3-b][1,4]benzodiazepin-6-one 5.8 gm of 11-chloroacetyl-5,11-dihydro-6H-pyrido[2,3-b][1,4]benzodiazepin-6-one, 3 ml of triethylamine and 4.2 gm of 1-(α-methyl benzyl)-piperazine ($R_1$= 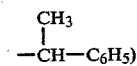)

were stirred in 40 ml of dioxane for 2 hours at 80° C. The dark solution was then evaporated in vacuo, and the residue was taken up in chloroform/water and shaken. The organic phase was then clarified with activated charcoal, dried with sodium sulfate and evaporated in vacuo. The residue was recrystallized from a mixture of ethyl acetate and cyclohexane.

M.p.: 204°–206° C.
Yield: 62% of theory.

EXAMPLE 8

5,11-Dihydro-11-{[4-(2-morpholino-ethyl)-1-piperazinyl]acetyl}-6H-pyrido[2,3-b][1,4]benzodiazepin-6-one was prepared from 8.62 gm of 11-chloroacetyl-5,11-dihydro-6H-pyrido-[2,3-b][1,4]benzodiazepin-6-one, 3.5 gm of sodium carbonate and 6.1 gm of 1-(2-morpholino-ethyl)piperazine in 100 ml of absolute ethanol in analogy to Example 1.

M.p.: 227°–229° C. (from n-propanol).
Yield: 63% of theory.

EXAMPLE 9

11-{[4-(1-Adamantyl-methyl)-1-piperazinyl]acetyl}-5,11-dihydro-6-H-pyrido[2,3-b][1,4]benzodiazepin-6-one 4.4 gm of 11-chloroacetyl-5,11-dihydro-6H-pyrido[2,3-b][1,4]benzodiazepin-6-one, 1.8 gm of sodium carbonate and 3.75 gm of 1-(1-adamantyl-methyl)-piperazine were reacted in 80 ml of absolute ethanol and worked up in analogy to Example 1. After recrystallization from a mixture of n-propanol and dimethylformamide; M.p.: 284°–287° C. (decomposition).

Yield: 64% of theory.

EXAMPLE 10

5,11-Dihydro-11-{[4-(3,4-methylenedioxy-benzyl)-1-piperazinyl]-acetyl}-6H-pyrido[2,3-b][1,4]benzodiazepin-6-one 8 gm of 11-chloroacetyl-5,11-dihydro-6H-pyrido[2,3-b][1,4]benzodiazepi-6-one and 14 gm of 1-(3,4- methylenedioxylbenzyl)-piperazine were refluxed in 400 ml of absolute benzene for 18 hours. The cooled reaction mixture was then admixed with ethanol, made alkaline with ammonia, and evaporated in vacuo. The residue was recrystallized from aqueous isopropanol and subsequently from isopropanol.

M.p.: 192°–193° C.
Yield: 51% of theory.

EXAMPLE 11

5,11-Dihydro-11-[(2,4-dimethyl-1-piperazinyl)acetyl]-6H-pyrido-[2,3-b][1,4]benzodiazepin-6-one-hydrochloride 8.6 gm of 11-chloroacetyl-5,11-dihydro-6H-pyrido[2,3-b][1,4]benzodiaze-pin-6-one, 3.1 gm of sodium carbonate and 4.5 gm of 1,3-dimethyl-piperazine were refluxed in 100 ml of absolute ethanol for 3.5 hours. After suction filtration the filtrate was evaporated to dryness. The residue was then purified on a silica gel column. The obtained base was dissolved in ethanol by addition of hydrochloric acid to form the hydrochloride. After recrystallization from ethanol: M.p.: 301°–303° C.
Yield: 20% of theory.

EXAMPLE 12

5,11-Dihydro-5-methyl-11-{[4-(3,4methylenedioxy-benzyl)-1-piperazinyl]acetyl}-6H-pyrido[2,3-b][1,4]benzodiazepin-6-one 10.5 gm of 11-chloroacetyl-5,11-dihydro-5-methyl-6H-pyrido[2,3-b]-[1,4]benzodiazepine-6-one, 3.8 gm of sodium carbonate and 8 gm of 1-[(3,4-methylenedioxy)-benzyl]-piperazine were reacted in 200 ml of absolute ethanol and worked up in analogy to Example 1.

M.p.: 200°–202° C.
Yield: 52% of theory.

EXAMPLE 13

11-[(4-Cyclohexylmethyl-1-piperazinyl)acetyl]-5,11-dihydro-6H-pyrido[2,3-b][1,4]benzodiazepin-6-one dihydrate by method B 5.05 gm of 5,11-dihydro-11-[(1-piperazinyl)acetyl]-6H-pyrido[2,3-b]-[1,4]benzodiazepin-6-one, 2.07 ml of triethylamine and 2.5 ml of cyclohexymethyl bromide were refluxed for 16 hours in 150 ml of absolute ethanol. After evaporating the reaction mixture, the residue was purified on a silica gel column and recrystallized from ethanol. The dihydrate was obtained: M.p.: 222°–224° C.

Yield: 33% of theory.

EXAMPLE 14

5,11-Dihydro-11-[(4-farnesyl-1-piperazinyl)acetyl]-6H-pyrido-[2,3-b][1,4]benzodiazepin-6-one dihydrochloride 8.4 gm of 5,11-dihydro-11-[(1-piperazinyl)acetyl]-6H-pyrido[2,3-b]-[1,4]benzodiazepin-6-one, 3.45 ml of triethylamine and 10.5 gm of farnesyl bromide were refluxed in 140 ml of n-propanol for 6 hours. The reaction mixture then was evaporated, and the residue dissolved in chloroform/water. The organic phase was dried with sodium sulfate, the chloroform was distilled off, and the residue was purified on a silica gel column. The obtained base was dissolved in isopropanol, and concentrated hydrochloric acid was added. The crystallized dihydrochloride was recrystallized from absolute ethanol and melted at 164°–170° C. (decomposition).

Yield: 29% of theory.

EXAMPLE 15

11-[(4-Cinnamyl-1-piperazinyl)acetyl]-5,11-dihydro-6H-pyrido-[2,3-b][1,4]benzodiazepin-6-one 5.05 gm of 5,11-dihydro-11-[(1-piperazinyl)acetyl]-6H-pyrido-[2,3-b][1,4]benzodiazepin-6-one, 1.6 gm of sodium carbonate and 3.7 gm of cinnamyl bromide were refluxed in 80 ml of n-propanol for 3.5 hours. After evaporation, the residue was dissolved in chloroform/water. The organic phase was dried with sodium sulfate, the chloroform was distilled off, and the residue was purified on a silica gel column. After recrystallization from ethyl acetate.

M.p.: 196°–198° C.
Yield: 41% of theory.

Using procedures analogous to those described in Examples 1–15, the compounds listed in the following table were also prepared:

| Example No. | $R_1$ | $R_2$ | $R_3$ | $R_4$ | M.p. (recryst.) | Yield % of theory | Prepared acc. to Example |
|---|---|---|---|---|---|---|---|
| 16 | —CH$_2$—CH$_2$—CH$_3$ | H | H | H | Dihydrochloride: 252°–254° C., (decomp.) (aqueous Isopropanol) | 51 | 1 |
| 17 | —CH(CH$_3$)$_2$ | H | H | H | Dihydrochloride: 239°–241° C., (decomp.) (absol. ethanol) | 44 | 1 |
| 18 | —CH$_2$—CH$_2$—CH$_2$—CH$_3$ | H | H | H | Dihydrochloride: 240°–242° C., (decomp.) (ethanol) | 53 | 5 |
| 19 | —CH(CH$_3$)—CH$_2$—CH$_3$ | H | H | H | Dihydrochloride-hydrate 210°–213° C. (absol. ethanol) | 48 | 14 |
| 20 | —CH$_2$—CH(CH$_3$)$_2$ | H | H | H | Dihydrochloride: 235°–237° C. (methanol) | 52 | 1 |
| 21 | —(CH$_2$)$_4$—CH$_3$ | H | H | H | Dihydrochloride: 242°–245° C. (methanol) | 32 | 1 |

-continued

| Example No. | $R_1$ | $R_2$ | $R_3$ | $R_4$ | M.p. (recryst.) | Yield % of theory | Prepared acc. to Example |
|---|---|---|---|---|---|---|---|
| 22 | $-CH(CH_3)-CH_2-CH_2-CH_3$ | H | H | H | Dihydrochloride-dihydrate: 226°–229° C. (methanol) | 46 | 1 |
| 23 | $-CH(CH_3)-CH_2-CH_2-CH_3$ | $CH_3$ | H | H | 130°–131° C. (cyclohexane) | 82 | 1 |
| 24 | $-CH_2-CH_2-CH(CH_3)CH_3$ | H | H | H | Dihydrochloride: 243°–245° C. (isopropanol) | 72 | 1 |
| 25 | $-(CH_2)_5-CH_3$ | H | H | H | Dihydrochloride: 239°–241° C. (decomp.) (ethanol) | 44 | 14 |
| 26 | $-CH_2-C(CH_3)_3$ | $CH_3$ | H | H | 136°–138° C. (cyclohexane) | 24 | 14 |
| 27 | $-(CH_2)_3-CH(CH_3)_2$ | H | H | H | Dihydrochloride-hydrate: 246°–248° C. (decomp.) (methanol) | 73 | 14 |
| 28 | $-CH_2-CH(C_2H_5)_2$ | H | H | H | Dihydrochloride: 232°–234° C. (ethanol) | 41 | 14 |
| 29 | $-CH_2-CH_2-C(CH_3)_3$ | H | H | H | Dihydrochloride: 235°–237° C. (methanol) | 61 | 1 |
| 30 | $-(CH_2)_6-CH_3$ | H | H | H | Dihydrochloride-dihydrate: 228°–230° C. (decomp.) (methanol) | 56 | 14 |
| 31 | $-(CH_2)_{11}-CH_3$ | H | H | H | Dihydrochloride: 195°–198° C. (decomp.) (ethanol) | 42 | 14 |
| 32 | $-CH_3$ | H | 3-$CH_3$ | H | Dihydrochloride: 257°–259° C. (methanol) | 62 | 1 |
| 33 | $-CH_3$ | H | 3-$CH_3$ | 5-$CH_3$ | Dihydrochloride: 253°–255° C. (methanol) | 60 | 1 |
| 34 | $-CH_3$ | H | 3-$CH_3$ | 6-$CH_3$ | Hydrochloride: 275°–276° C. (isopropanol) | 33 | 1 |
| 35 | $-CH_2-CH(cyclopropyl)$ | H | H | H | Dihydrochloride: 233°–235° C. (ethanol) | 70 | 14 |
| 36 | $-CH_2-CH(cyclopropyl)$ | $CH_3$ | H | H | 135°–136° C. (cyclohexane) | 43 | 14 |
| 37 | $-CH(cyclopentyl)$ | H | H | H | 218°–220° C. (ethyl acetate) | 20 | 1 |
| 38 | $-CH_2-(cyclohexyl)$ | H | H | H | 248°–250° C. (ethanol) | 34 | 1 |
| 39 | $-CH_2-CH=CH_2$ | $CH_3$ | H | H | 164°–166° C. (acetonitrile) | 33 | 14 |
| 40 | $-CH_2-C\equiv CH$ | H | H | H | 248°–250° C. (n-propanol) | 61 | 13 |
| 41 | $-CH_2-C(CH_3)=CH_2$ | $CH_3$ | H | H | 135°–140° C. hydrochloride: 250°–252° C. (decomp.) (dimethylformamide) | 65 | 1 |
| 42 | $-CH(CH_3)-CH=CH_2$ | H | H | H | 140°–142° C. (ethyl acetate/cyclohexane) | 51 | 1 |

-continued

| Example No. | R₁ | R₂ | R₃ | R₄ | M.p. (recryst.) | Yield % of theory | Prepared acc. to Example |
|---|---|---|---|---|---|---|---|
| 43 | —(CH₂)₃—CH=CH₂ | H | H | H | dihydrochloride-hydrate: 216°–218° C. (abs. ethanol) | 62 | 14 |
| 44 | —CH₂—CH=C(CH₃)₂ | CH₃ | H | H | dihydrochloride: 229°–233° C. (decomp.) (abs. ethanol) | 58 | 1 |
| 45 | —(CH₂)₄—CH=CH₂ | H | H | H | dihydrochloride-hydrate 231°–234° C. (decomp.) (methanol) | 40 | 13 |
| 46 | —CH₂—CH=C(CH₃)—CH₂—CH₂—CH=C(CH₃)—CH₃ (Geranyl) | H | H | H | dihydrochloride: 188°–190° C. (decomp.) (abs. ethanol) | 71 | 1 |
| 47 | —CH₂—CH₂—CH(CH₃)—CH₂—CH₂—CH=C(CH₃)—CH₃ (Citronellyl) | H | H | H | Dihydrochloride: 200°–204°C. (decomp.) (ethanol) | 68 | 1 |
| 48 | —CH₂—CH=C(CH₃)—CH₂—CH₂—CH=C(CH₃)—CH₂—CH=C(CH₃)—CH₃ (Farnesyl) | CH₃ | H | H | Dihydrochloride: 208°–210° C. (isopropanol) | 61 | 1 |
| 49 | —CH₂—CH=C(CH₃)—(CH₂)₃—CH(CH₃)—(CH₂)₃—CH(CH₃)—CH₂—CH(CH₃)₂ (Phytyl) | CH₃ | H | H | Dihydrochloride: 180° C. (decomp.) (abs. ethanol) | 75 | 1 |
| 50 | —(CH₂)₃—N(piperazinyl)N—CH₃ | H | H | H | 194°–197° C. (ethyl acetate) | 36 | 15 |
| 51 | —CH₂—(2-chlorophenyl) | H | H | H | 238°–240° C. (n-propanol) | 61 | 5 |
| 52 | —CH₂—(indanyl) | H | H | H | Dihydrochloride-hydrate: 209°–212° C. (ethanol) | 47 | 14 |
| 53 | —CH₂—CH₂—C₆H₅ | H | H | H | Hydrochloride: 263°–264° C. (n-propanol) | 68 | 7 |
| 54 | —CH₂—CH₂—C₆H₅ | CH₃ | H | H | 173°–175° C. (n-propanol) | 67 | 7 |
| 55 | —(CH₂)₃—C₆H₅ | H | H | H | 210°–212° C. (n-propanol) | 64 | 1 |

Purification of the raw product was carried out in all examples on a silica gel column with a mixture of chloroform, methanol, cyclohexane and concentrated ammonia in a proportion of 68:15:15:2 as solvent and eluent.

The compounds of the present invention, that is, those embraced by formula I above and their non-toxic, pharmacologically acceptable addition salts, have useful pharmacodynamic properties. More particularly, they exhibit anti-ulcerogenic and secretion inhibiting activities in warm-blooded animals, such as mice and rats. Thus, the compounds of the present invention are useful for the treatment of gastric and duodenal ulcers, gastritis and similar diseases of the stomach and intestines.

The above pharmacological properties of the compounds of this invention were ascertained by the methods described below, and the tables show the results of these tests for a few representative species, where

| | |
|---|---|
| 5,11-dihydro-11-{[4-(2-methyl-allyl)-1-piperazinyl]-acetyl}-6H-pyrido [2,3-b][1,4] benzodiazepin-6-one | = A |
| 5,11-dihydro-11-{[4-(3-methyl-but-2-enyl)-1-piperazinyl]acetyl}-6H-pyrido [2,3-b][1,4] benzodiazepin-6-one dihydrochloride | = B |
| 5,11-dihydro-11-{[4-(2,2-dimethy-propyl)-1-piperazinyl]acetyl}-6H-pyrido[2,3-b][1,4]benzodiazepin-6-one | = C |
| 11-{[4-(1-adamantyl-methy)-1-piperazinyl]acety}-5,11-dihydro-6H-pyrido[2,3-b][1,4]benzodiazepin-6-one | = D |
| 5,11-dihydro-11-{[4-(3,4-methylenedioxy benzyl)-1-piperazinyl] acetyl}-6H-pyrido [2,3-b][1,4] benzodiazepin-6-one | = E |
| 5,11-dihydro-11-[(2,4-dimethyl-1-piperazinyl)-acetyl]-6H-pyrido[2,3-b][1,4]benzodiazepin-6-one hydrochloride | = F |
| 5,11-dihydro-5-methyl-11-{[4-(3,4-methylene-dioxy-benzyl-1-piperazinyl]acetyl}-6H-pyrido-[2,3-b][1,4]benzodiazepin-6-one | = G |
| 11-[(4-cinnamyl-1-piperazinyl)acetyl]-5,11-dihydro-6H-pyrido[2,3-b][1,4]benzodiazepin-6-one | = H |

The compounds were examined with regard to their inhibiting effect on the formation of stress ulcers in rats and their spasmolytic effect, related to atropine, with consideration of their acute toxicity.

The inhibiting effect on the formation of stress ulcers in rats was determined according to the method of K. Takagi and S. Okabe, Jap.Journ.Pharmac. 18,pp. 9 to 18 (1968). Fed female rats with a body weight between 220 and 260 gm were individually put into small wire cages and were subsequently kept vertically submerged in a water bath which was kept constant at a temperature of 23° C. for 16 hours, so that only the heads and the breastbones of the animals were above the water surface. The test compounds were administered perorally 5 to 10 minutes before. With each substance five animals were treated. 1 ml of a 0.9% physiological sodium chloride solution or 1 ml of a 1% tylose solution was administered to the control animals in the same way. After 18 hours the animals were killed by an overdose of ethyl chloride, the stomachs were excised, cut along the big curvature and spread on a cork plate. The evaluation was carried out according to the methods of Marazzi-Uberti and Turba, Med. Exp. 4, pp. 284 to 292 (1961), and Takagi and Okabe (supra)

The spasmolytic effect was determined in vitro on the guinea pig colon, using the experimental arrangement according to R. Magnus, Pflügers Archiv, 102, pp. 123 (1904). Acetylcholine was taken to induce spasms, the substance for comparison was atropinesulfate. The spasticum was administered one minute before the administration of the spasmolytic substance, and the spasmolytic was allowed to take effect for 1 minute. In rats it was also observed that the atropine-like side-effects, such as inhibition of salivary secretion, were completely missing or remarkably decreased when the substances A to H were administered.

The acute toxicity was determined after peroral administration of the test substance to fasted white mice with a body weight of 18 to 20 gm. The observation period was 14 days. For each dosage a group of six mice was used.

| Compound | Ulcer inhibition in % (rat) after peroral administration of | | | Spasmolysis (acetyl-choline) in respect to Atropine = 1 | $LD_{50}$ peroral mgm/kg mouse |
|---|---|---|---|---|---|
| | 50 | 25 | 12.5 | | |
| | mgm/kg | | | | |
| A | 90 | 52 | 32 | 1/330 | >3000+ |
| B | 84 | 63 | 52 | 1/200 | >1500+ |
| C | 95 | 61 | 39 | 1/70 | >1500+ |
| D | 79 | 47 | 26 | 1/86 | >3000+ |
| E | 95 | 73 | 37 | 1/78 | >3000+++ |
| F | 95 | 90 | 84 | 1/130 | >3000++ |
| G | 90 | 58 | 21 | 1/290 | >1500+++ |
| H | 95 | 69 | 53 | 1/700 | ~3000++++ |

+ means, 0 of 6 animals died;
++ means, 1 of 6 animals died;
+++ means, 2 of 6 animals died;
++++ means, 4 of 6 animals died;

The spasmolytic effect of the compounds A to H in comparison to that of atropine sulfate is remarkably weaker, and therefore also the atropine-like side-effects.

For pharmaceutical purposes the compounds of the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective oral dosage unit of the compounds according to the present invention is from 0.083 to 0.83 mgm/kg body weight, preferably 0.16 to 0.5 mgm/kg body weight. The daily dose rate is 0.3 to 1.7 mgm/kg, preferably 0.5 to 1.5 mgm/kg.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 56

Tablets

The tablet composition is compounded from the following ingredients:

| | |
|---|---|
| 5,11-Dihydro-11-{[4(2-methyl-allyl)-1-piperazinyl]acetyl}-6H-pyrido[2,3-b][1,4]benzodi-azepin-6-one | 10.0 parts |
| Lactose | 148.0 parts |
| Potato starch | 60.0 parts |
| Magnesium stearate | 2.0 parts |
| Total | 220.00 parts |

Preparation

An aqueous 10% slurry is prepared by heating a portion of the potato starch. The active ingredient, the lactose and the remaining potato starch admixed with each other, and the mixture is granulated by passing it, together with the above slurry, through a 1.5 mm mesh screen. The granulate is dried at 45° C., again passed through the screen, admixed with the magnesium stearate, and the composition is compressed into 220 mgm-tablets. Each tablet is an oral dosage unit composition containing 10 mgm of the active ingredient.

EXAMPLE 57

Coated pills 220 mgm-pill cores are prepared from the same ingredients and in the same manner as in Example 56. The pill cores are then coated with a thin shell consisting essentially of talcum and sugar, and finally polished with beeswax in conventional manner.

EXAMPLE 58

Hypodermic solution

The solution is compounded from the following ingredients:

| | |
|---|---|
| 5,11-Dihydro-11-{[4-(3-methyl-but-2-enyl)-1-piperazinyl]-acetyl}-6H-pyrido [2,3-b]-[1,4]benzodiazepin-6-one dihydrochloride | 2.0 parts |
| Sodium chloride | 8.0 parts |
| Distilled water q.s.ad | 1000.0 parts by vol. |

Preparation

The active ingredient and the sodium chloride are dissolved in a sufficient amount of distilled water, and the solution is diluted with additional distilled water to the indicated volume. The solution is then filtered until free from suspended particles and subsequently filled into 1 cc-ampules, which are finally sterilized at 120° C. for 20 minutes and sealed. The contents of each ampule are an injectable solution containing 2 mgm of the active ingredient.

EXAMPLE 59

Suppositories

The suppository composition is compounded from the following ingredients:

| | |
|---|---|
| 5,11-Dihydro-11-{[4-(2,2-dimethyl-propyl)-1-piperazinyl]acetyl}-6H-pyrido[2,3-b][1,4]benzodiazepin-6-one | 15.0 parts |
| Suppository base (e.g. cocoa butter) | 1685.0 parts |
| Total | 1700.0 parts |

Preparation

The suppository base is melted and cooled to 40° C., the milled active ingredient is homogeneously dispersed therein, the mixture is cooled to 37° C., and 1700 mgm portions thereof are poured into cooled suppository molds and allowed to harden therein. Each suppository is a rectal dosage unit composition containing 15 mgm of the active ingredient.

EXAMPLE 60

Drop solution

The solution is compounded from the following ingredients:

| | |
|---|---|
| 5,11-Dihydro-11-{[4-(3-methyl-but-2-enyl)-1-piperazinyl]acetyl}-6H-pyrido[2,3-b][1,4]benzodiazepin-6-one-dihydrochloride | 1.0 parts |
| Methyl p-hydroxy-benzoate | 0.035 parts |

-continued

| | |
|---|---|
| Propyl p-hydroxy-benzoate | 0.015 parts |
| Oil of anise | 0.05 parts |
| Menthol | 0.06 parts |
| Ethanol, pure | 10.0 parts |
| Sodium cyclamate | 1.0 parts |
| Glycerin | 15.0 parts |
| Distilled water q.s. ad | 100.0 parts by vol. |

Preparation

The active ingredient and the sodium cyclamate are dissolved in about 70 parts by volume of water, and the glycerin is added to the solution. The p-hydroxybenzoates, the oil of anise and the menthol are dissolved in the ethanol, and the solution is added to the aqueous solution while stirring. The mixed solution is diluted with distilled water to the indicated volume, and is then filtered until free from suspended particles. 1 ml (20 drops) of the filtrate is an oral dosage unit composition containing 10 mgm of the active ingredient.

Any one of the other pyridobenzodiazepinones embraced by formula I or a non-toxic, pharmacologically acceptable acid addition salt thereof may be substituted for the particular pyridobenzodiazepinone compound in Examples 56 through 60. Likewise, the amount of ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

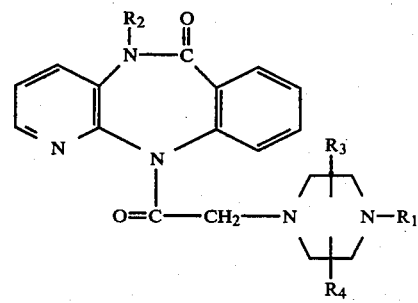

wherein
$R_1$ is alkyl of 3 to 12 carbon atoms; olefinic hydrocarbyl of 3 to 20 carbon atoms having 1 to 3 double bonds; methylenedioxy-benzyl; phenyl-(alkenyl of 2 to 4 carbon atoms); (cycloalkyl of 5 to 7 carbon atoms) - methyl; adamantylmethyl; or, when $R_3$ and/or $R_4$ are methyl or ethyl, also methyl or ethyl;
$R_2$ is hydrogen or methyl; and
$R_3$ and $R_4$ are each hydrogen, methyl or ethyl;
or a non-toxic, pharmacologically acceptable acid addition salt thereof.

2. A compound of claim 1, which is 5,11-dihydro-11{[4-(2-methyl-allyl)-1-piperazinyl]acetyl}-6H-

3. A compound of claim 1, which is 5,11-dihydro-11-{[4-(3-methyl-but-2-enyl)-1-piperazinyl]-acetyl}-6H-pyrido[2,3-b][1,4]benzodiazepin-6-one or a non-toxic, pharmacologically acceptable acid addition salt thereof.

4. A compound of claim 1, which is 5,11-dihydro-11-{[4-(2,2-dimethyl-propyl)-1-piperazinyl]-acetyl}-6H-pyrido[2,3-b][1,4]benzodiazepin-6-one or a non-toxic, pharmacologically acceptable acid addition salt thereof.

5. A compound of claim 1, which is 11-{[4-(1-adamantyl-methyl)-1-piperazinyl]acetyl}-5,11-dihydro-6H-pyrido[2,3-b][1,4]benzodiazepin-6-one or a non-toxic, pharmacologically acceptable acid addition salt thereof.

6. A compound of claim 1, which is 5,11-dihydro-11-{[4-(3,4-methylenedioxy-benzyl)-1-piperazinyl]acetyl}-6H-pyrido[2,3-b][1,4]benzodiazepin-6-one or a non-toxic, pharmacologically acceptable acid addition salt thereof.

7. A compound of claim 1, which is 5,11-dihydro-11-[(2,4-dimethyl-1-piperazinyl)acetyl]-6H-pyrido[2,3-b][1,4]benzodiazepin-6-one or a non-toxic, pharmacologically acceptable acid addition salt thereof.

8. A compound of claim 1, which is 5,11-dihydro-5-methyl-11{[4-(3,4-methylenedioxy-benzyl)-1-piperazinyl]acetyl}-6H-pyrido[2,3-b][1,4]benzodiazepin-6-one or a non-toxic, pharmacologically acceptable acid addition salt thereof.

9. A compound of claim 1, which is 11-[(4-cinnamyl-1-piperazinyl)acetyl]-5,11-dihydro-6H-pyrido[2,3-b][1,4]benzodiazepin-6-one or a non-toxic, pharmacologically acceptable acid addition salt thereof.

10. An anti-ulcerogenic or secretion-inhibiting pharmaceutical dosage unit composition consisting essentially of an inert pharmaceutical carrier and an effective anti-ulcerogenic or secretion-inhibiting amount of a compound of claim 1.

11. The method of treating gastro-intestinal ulcers or inhibiting gastro-intestinal secretion in a warm-blooded animal, which comprises perorally, parenterally or rectally administering to said animal an effective anti-ulcerogenic or secretion-inhibiting amount of a compound of claim 1.

* * * * *

UNITED STATES PATENT AND TRADEMARK OFFICE
CERTIFICATE OF CORRECTION

PATENT NO. : 4,213,984
DATED : July 22, 1980
INVENTOR(S) : GÜNTHER SCHMIDT, MATYAS LEITOLD It is certified that error appears in the above-identified patent and that said Letters Patent are hereby corrected as shown below:

Column 6, line 68: "benzodiazepi-6" should read -- benzodiazepin-6 --.

Column 13, line 15: "methy)-piperazinyl]acety}-" should read -- methyl)-piperazinyl]acetyl}- --.

Column 15, line 21: "g.s.ad" should read -- q.s.ad --.

Column 16, line 61: "adamantylmethyl" should read -- adamantyl-methyl --.

Signed and Sealed this

Eleventh Day of November 1980

[SEAL]

Attest:

SIDNEY A. DIAMOND

Attesting Officer

Commissioner of Patents and Trademarks